US007003001B2

(12) United States Patent
Sharma et al.

(10) Patent No.: US 7,003,001 B2
(45) Date of Patent: Feb. 21, 2006

(54) MEDICAL LASER APPARATUS

(75) Inventors: Lalit B. Sharma, Gamagori (JP); Kenichi Hayashi, Gamagori (JP)

(73) Assignee: Nidex Co., Ltd., Gamagori (JP)

( * ) Notice: Subject to any disclaimer, the term of this patent is extended or adjusted under 35 U.S.C. 154(b) by 101 days.

(21) Appl. No.: 10/828,319

(22) Filed: Apr. 21, 2004

(65) Prior Publication Data

US 2004/0213301 A1    Oct. 28, 2004

(30) Foreign Application Priority Data

Apr. 25, 2003    (JP)    ............... 2003-120944

(51) Int. Cl.
    *H01S 3/30*    (2006.01)
(52) U.S. Cl. ............................. 372/3; 372/6
(58) Field of Classification Search .......... 372/3, 372/6
    See application file for complete search history.

(56) References Cited

U.S. PATENT DOCUMENTS

| | | | |
|---|---|---|---|
| 5,796,761 A * | 8/1998 | Injeyan et al. ............... | 372/3 |
| 5,815,518 A * | 9/1998 | Reed et al. .................. | 372/6 |
| 6,636,537 B1 * | 10/2003 | Takada ........................ | 372/23 |
| 6,844,963 B1 * | 1/2005 | Iketaki et al. ............... | 359/368 |
| 6,901,084 B1 * | 5/2005 | Pask et al. ................... | 372/3 |

| | | | |
|---|---|---|---|
| 2005/0143720 A1 * | 6/2005 | Yamada et al. .............. | 606/10 |
| 2005/0163426 A1 * | 7/2005 | Fermann et al. ............. | 385/37 |

FOREIGN PATENT DOCUMENTS

| | | |
|---|---|---|
| DE | 40 29 530 A1 * | 3/1992 |
| EP | 0 867 151 A2 * | 9/1998 |
| EP | 0 867 151 A3 * | 9/1998 |
| EP | 1 241 746 A1 * | 9/2002 |
| JP | A 63-195628 | 8/1988 |
| JP | A 11-54853 | 2/1999 |
| JP | A 2002-151774 | 5/2002 |

* cited by examiner

*Primary Examiner*—Wilson Lee
*Assistant Examiner*—Leith A. Al-Nazer
(74) *Attorney, Agent, or Firm*—Oliff & Berridge, PLC

(57) ABSTRACT

A medical laser apparatus comprises: a solid laser oscillating source which emits a beam of a wavelength λ1 in an infrared region of approx. 1040 nm to approx. 1080 nm; a first fiber-based Raman shifter including a first Raman fiber which generates, when receives the λ1-beam from the laser oscillating source, a first-order Stokes beam of a wavelength λ2 different from the wavelength λ1 by stimulated Raman scattering, the first Raman fiber being formed with a pair of fiber Bragg gratings which forms a resonator for the λ2-beam; a first nonlinear crystal which wavelength-converts the λ2-beam outputted from the first Raman wavelength shifter to a second harmonic beam of a wavelength λ2' in an orange region of approx. 580 nm to approx. 600 nm; and a light guiding optical system which guides the λ2'-beam to a treatment part.

8 Claims, 5 Drawing Sheets

MEDICAL LASER APPARATUS

BACKGROUND OF THE INVENTION

1. Field of the Invention

The present invention relates to a medical laser apparatus which is used in an ophthalmic hospital and others.

2. Description of Related Art

As medical laser apparatuses (e.g., for ophthalmic treatments), there have been known apparatus using a krypton laser, a dye laser, a frequency doubled Nd:YAG laser which is a solid laser, or the like. For example, the krypton laser can generate green laser beams of wavelengths of approx. 520 nm and approx. 530 nm, a yellow laser beam of a wavelength of approx. 568 nm, and a red laser beam of a wavelength of approx. 647 nm. The dye laser can generate yellow to red laser beams of wavelengths of approx. 575 nm to approx. 630 nm. The frequency doubled Nd:YAG laser can generate second harmonics, that is, a green laser beam of a wavelength of approx. 532 nm, a yellow laser beam of a wavelength of approx. 561 nm, and a red laser beam of a wavelength of approx, 659 nm.

For medical treatments, a laser beam of a wavelength (namely, color) selected according to a treatment part, a treatment purpose, and others is used. For an ophthalmic photocoagulation treatment, for example, yellow to orange laser beams are preferably used for providing a good coagulation efficiency even at low energy. In the case where a patient's eye is bleeding at the fundus or an optic media to the fundus is opaque, a red laser beam is preferably used.

The apparatuses using the krypton laser or the dye laser have many disadvantages; a short life of a laser tube, large electric power requirements, and an increase in apparatus size. On the other hand, the apparatuses using the solid laser such as the frequency doubled Nd:YAG laser could reduce these disadvantages but could not generate an orange laser beam suitable for photocoagulation. Further, as the red laser beam, a beam of a wavelength shorter than approx. 659 nm is preferable.

SUMMARY OF THE INVENTION

The present invention has been made in view of the above circumstances and has an object to overcome the above problems and thus provide a medical laser apparatus which can have a long life, low electric power requirements, and a reduced size, and which is capable of generating laser beams of wavelengths (colors) suitable for medical treatments.

Additional objects and advantages of the invention will be set forth in part in the description which follows and in part will be obvious from the description, or may be learned by practice of the invention. The objects and advantages of the invention may be realized and attained by means of the instrumentalities and combinations particularly pointed out in the appended claims.

To achieve the purpose of the invention, there is provided a medical laser apparatus comprising: a solid laser oscillating source which emits a beam of a wavelength $\lambda 1$ in an infrared region of approx. 1040 nm to approx. 1080 nm; a first fiber-based Raman shifter including a first Raman fiber which generates, when receives the $\lambda 1$-beam from the laser oscillating source, a first-order Stokes beam of a wavelength $\lambda 2$ different from the wavelength $\lambda 1$ by stimulated Raman scattering, the first Raman fiber being formed with a pair of fiber Bragg gratings which forms a resonator for the $\lambda 2$-beam; a first nonlinear crystal which wavelength-converts the $\lambda 2$-beam outputted from the first Raman wavelength shifter to a second harmonic beam of a wavelength $\lambda 2'$ in an orange region of approx. 580 nm to approx. 600 nm; and a light guiding optical system which guides the $\lambda 2'$-beam to a treatment part.

BRIEF DESCRIPTION OF THE DRAWINGS

The accompanying drawings, which are incorporated in and constitute a part of this specification illustrate an embodiment of the invention and, together with the description, serve to explain the objects, advantages and principles of the invention.

In the drawings.

DETAILED DESCRIPTION OF THE PREFERRED EMBODIMENTS

Figure 1:
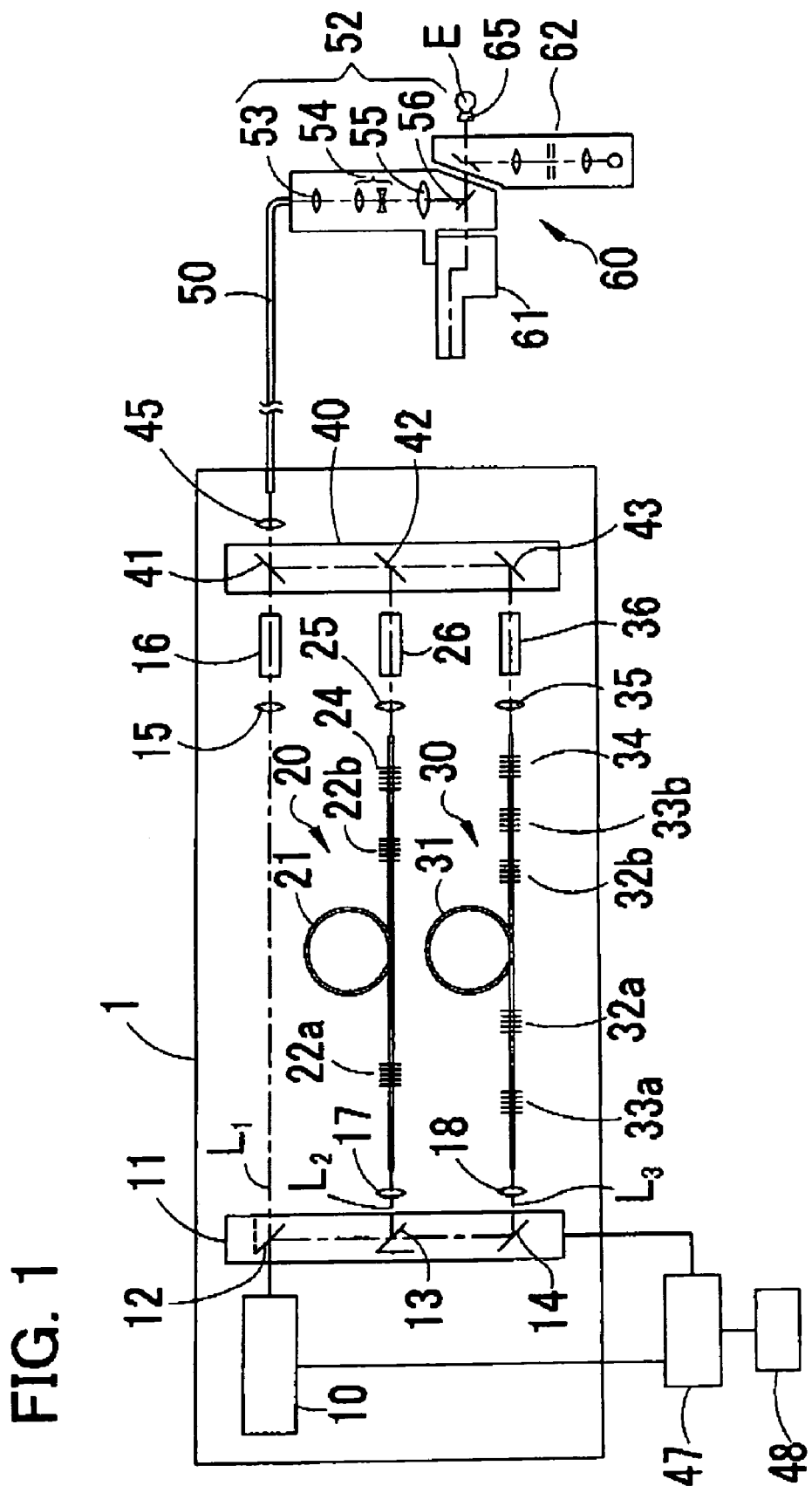
FIG. 1 is a schematic structural view of a laser apparatus for an ophthalmic treatment in a first embodiment.

A detailed description of preferred embodiments of the present invention will now be given referring to the accompanying drawings. FIG. 1 is a schematic structural view of a laser apparatus for an ophthalmic treatment in a first embodiment.

In FIG. 1, a laser oscillator 1 which emits a laser beam is internally provided with a laser oscillating source 10 which emits a linearly polarized infrared beam. This laser oscillating source 10 is for example an Nd:YAG laser which is a laser diode pump and emits a fundamental-wave infrared beam of a wavelength $\lambda 1$ (approx. 1064 nm). An input switching unit 11 selectively directs the beam of the wavelength $\lambda 1$ (hereinafter, referred to as "$\lambda 1$-beam") emitted from the laser oscillating source 10 to a first optical path L1, a second optical path L2, or a third optical path L3. This input switching unit 11 is constructed of for example a mirror 12 placed in the optical path L1 and mirrors 13 and 14 placed in order in an optical path formed in a reflecting direction of the mirror 12. The mirrors 12 and 13 are moved to respective positions shown by broken lines out of the associated optical paths.

When the mirror 12 is moved out of the optical path, the linearly polarized $\lambda 1$-beam is directed to the optical path L1. In this optical path L1 there are disposed a condensing lens 15 and a first periodically-poled nonlinear crystal (corresponding to a "second nonlinear crystal" in claims) 16 such as PPLN with its Z axis aligned parallel to the polarization plane of the linearly polarized λ1-beam (hereinafter, referred to as "PPLN"). The λ1-beam is wavelength-converted to a second-harmonic green beam of a wavelength λ1' (approx. 532 nm) by the first nonlinear crystal 16.

When both mirrors 12 and 13 are set in the optical path, the λ1-beam is directed to the optical path L2. In the optical path L2, there are placed a condensing lens 17, a fiber-based Raman wavelength shifter (converter) 20, a condensing lens 25, and a second periodically-poled nonlinear crystal (corresponding to a "first nonlinear crystal" in claims) 26 such as PPLN. The Raman wavelength shifter (converter) 20 is constructed of a single mode polarization presenting optical fiber (a nonlinear optical fiber) 21 having a silica($SiO_2$)-based core doped with titanium oxide ($TiO_2$). The optical fiber 21 is 6 μm in core diameter and approx. 500 m or more in length. This optical fiber 21 is formed with a pair of fiber Bragg gratings (hereinafter, FBG) 22a and 22b which forms a resonator for a first-order Stokes beam of a wavelength λ2 (approx. 1180 nm) generated by stimulated Raman scattering. In addition, at the output end of the optical fiber 21, an FBG 24 is formed to reflect the λ1-beam while allowing the beam of the wavelength λ2 (hereinafter, referred to as "λ2-beam") to pass therethrough.

Figure 2:
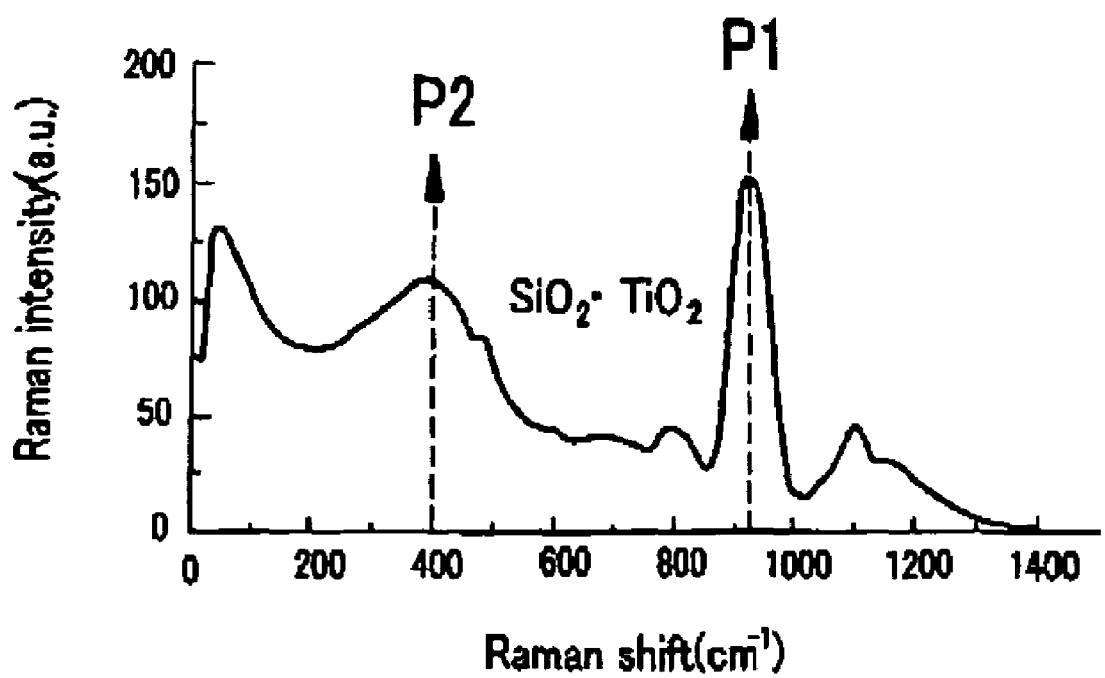
FIG. 2 is a graph showing stimulated Raman scattering characteristics of a Raman fiber used in the present invention.

FIG. 2 shows stimulated Raman scattering characteristics of the $TiO_2$-doped, $SiO_2$-based optical fiber. As shown in FIG. 2, the $TiO_2$-doped, $SiO_2$-based optical fiber provides peaks of the stimulated Raman scattering near about 925 $cm^{-1}$ and about 400 $cm^{-1}$, respectively. Accordingly, with an excitation beam of the wavelength λ1, there is caused the stimulated Raman scattering having a peak at λ2 corresponding to a Raman shift P1 of 925 $cm^{-1}$. That is, $$9398\ cm^{-1}\ (approx.\ 1064\ nm) - 925\ cm^{-1} \rightarrow 8473\ cm^{-1}\ (approx.\ 1180\ nm).$$

Thus, the first-order Stokes beam of the wavelength λ2 is generated. For this λ2 beam, the FBG 22a which has high reflectivity (99% or more reflectivity) and the FBG 22b which allows a part of light to pass (85% or less reflectivity) form a resonator, picking up the λ2-beam. The reflectivity of the FBG 22b that acts as an output coupler is so chosen as to achieve optimum output power at the λ2-beam. It is to be noted that the λ1-beam travels backward through the optical fiber 21 by the FBG 24, thereby enhancing the degree of the use of the λ1-beam.

The λ2-beam having passed the FBG 24 then passes through the condensing lens 25 and enters the second nonlinear crystal 26 in which the λ2-beam is wavelength-converted to a second-harmonic orange beam of a wavelength λ2' (approx. 590 nm).

When the mirror 12 is set in the optical path whereas the mirror 13 is moved out of the optical path, the λ1-beam is directed to the optical path L3. In the optical path L3, there are placed a condensing lens 18, a fiber-based Raman wavelength shifter (converter) 30, a condensing lens 35, and a third periodically-poled nonlinear crystal 36 such as PPLN. The Raman wavelength shifter (converter) 30 is constructed of a $TiO_2$-doped, $SiO_2$-based optical fiber 31 as with the optical fiber 21. The optical fiber 31 is 6 μm in core diameter and approx. 500 m or more in length. This optical fiber 31 is formed with a pair of FBGs 32a and 32b which forms a resonator for the first-order Stokes beam of the wavelength λ2 generated by the stimulated Raman scattering, and another pair of FBGs 33a and 33b which forms a resonator for a second-order Stokes beam of a wavelength λ3 (approx. 1240 nm) generated by the stimulated Raman scattering. At the output end of the optical fiber 31, an FBG 34 is formed to reflect the λ1-beam while allowing the beam of the wavelength λ3 (hereinafter, referred to as "λ3-beam") to pass therethrough.

As described above, the $SiO_2$-based optical fiber doped with $TiO_2$ provides a peak of the stimulated Raman scattering near about 400 $cm^{-1}$ in addition to near about 925 $cm^{-1}$. In the Raman wavelength shifter 30, accordingly, with the excitation beam of the wavelength λ1, the first-order Stokes beam of the wavelength λ2 is generated. For this λ2-beam, the FBGs 32a and 32b of high reflectivity form a resonator to therein confine (resonate) the λ2-beam. Subsequently, with the λ2-beam, the stimulated Raman scattering can be caused with a peak at λ3 corresponding to a Raman shift P2 of 408 $cm^{-1}$. That is, $$9398\ cm^{-1}\ (approx.\ 1064\ nm) - 925\ cm^{-1} - 408\ cm^{-1} \rightarrow 8065\ cm^{-1}\ (approx.\ 1240\ nm).$$

Thus, the second-order Stokes beam of the wavelength λ3 is generated. For this λ3-beam, the FBG 33a having high reflectivity (99% or more reflectivity) and the FBG 33b which allows a part of light to pass (85% or less reflectivity) form a resonator, picking up the λ3-beam. The reflectivity of the FBG 33b that acts as an output coupler is so chosen as to achieve optimum output power at the λ3-beam.

The λ3-beam having passed the FBG 34 then passes through the condensing lens 36 and enters the third nonlinear crystal 36 in which the λ3-beam is wavelength-converted to a second-harmonic red beam of a wavelength λ3' (approx. 620 nm).

The λ1'-, λ2'-, and λ3'-beams generated respectively as above are selectively outputted by an output switching unit 40. This output switching unit 40 includes for example dichroic mirrors 41 and 42 and a mirror 43. The dichroic mirror 42 allows the red beam of the wavelength λ3' to pass therethrough while reflecting the orange beam of the wavelength λ2'. The dichroic mirror 41 reflects the λ3'- and λ2'-beams while allowing the green beam of the wavelength λ1'. The beams outputted from the output switching unit 40 enters the optical fiber 50 through a condensing lens 45. It is to be noted that in each optical path between each of the nonlinear crystals 16, 26, and 36 and the condensing lens 45, an optical element (not illustrated) for adjusting the diameter of the respective beams is appropriately placed such that, through the condensing lens 45, each of the λ1'-, λ2'-, and λ3'-beams efficiently enter the optical fiber 50 of a light guiding optical system.

The output end of the optical fiber 50 is connected to a light guiding optical system 52 for guiding the beam to a patient's eye E. This optical system 52 is provided with a relay lens 53, a zoom lens 54 for changing a spot size of the beam, an objective lens 55, and a mirror 56 which reflects the beam toward the patient's eye E. This optical system 52 is mounted to a slit lamp 61 provided in a binocular microscope 61. The eye E is illuminated by an illumination part 62 provided in the slit lamp 60. For a photocoagulation treatment, the beam guided by the light guiding optical system 52 is applied to the fundus of the eye E through a contact lens 65.

The laser oscillating source 10 and the input switching unit 11 are connected to a control unit 47. This control unit 47 is connected to a control panel 48 having a switch for selecting a wavelength (color) of the beam.

The photocoagulation treatment using the above laser apparatus is performed as follows. An operator first selects a wavelength (color) to be used with the switch on the control panel 48 and then sets treatment conditions such as output power, photocoagulation time, etc. Upon receipt of a wavelength selecting signal from the control panel 48, the control unit 47 drives the mirrors 12 and 13 in the input switching unit 11 to switch among the optical paths. When "green" is selected, the beam from the laser oscillating source 10 is directed to the optical path L1, so that the laser oscillator 1 outputs the green beam. When "orange" is selected, the beam from the laser oscillating source 10 is guided to the Raman wavelength shifter 20 placed in the optical path L2, so that the laser oscillator 1 outputs the orange beam. When "red" is selected, the beam from the laser oscillating source 10 is guided to the Raman wavelength shifter 30 in the optical path L3, so that the laser oscillator 1 outputs the red beam.

In the above description, the Nd:YAG laser is used as the laser oscillating source 10, but an Nd:YLF laser may be used instead. This Nd:YLF laser emits a fundamental-wave infrared beam of a wavelength of approx. 1053 nm. When it is used as the excitation beam of the wavelength $\lambda 1$, the $\lambda 1$-beam is wavelength-converted in the following manners. In the case of the optical path L1, the $\lambda 1$-beam is converted by the first nonlinear crystal 16 to a second-harmonic green beam of the wavelength $\lambda 1'$ (approx. 527 nm). In the case of the optical path L2, the $\lambda 1$-beam is converted by the Raman wavelength shifter 20 as follows:

9496 cm$^{-1}$ (approx. 1053 nm)−925 cm$^{-1}$→8571 cm$^{-1}$ (approx. 1166 nm).

Thus, the first-order Stokes beam of the wavelength $\lambda 2$ (approx. 1166 nm) is generated. This $\lambda 2$-beam is then wavelength-converted by the second nonlinear crystal 26 to a second-harmonic orange beam having a wavelength $\lambda 2'$ (approx. 583 nm).

In the case of the optical path L3, the $\lambda 1$-beam is converted by the Raman wavelength shifter 30 as follows:

9496 cm$^{-1}$ (approx. 1053 nm)−925 cm$^{-1}$−408 cm$^{-1}$→8163 cm$^{-1}$ (approx. 1225 nm).

Thus, the second-order Stokes beam of the wavelength $\lambda 3$ (approx. 1225 nm) is generated. This $\lambda 3$-beam is then wavelength-converted by the third nonlinear crystal 36 to a second-harmonic red beam of a wavelength $\lambda 3'$ (approx. 613 nm).

For the photocoagulation treatment, it is preferable to output the green beam of a wavelength in a range of approx. 520 nm to approx. 540 nm. Therefore the wavelength $\lambda 1$ for generating the green beam of the wavelength $\lambda 1'$ in the aforesaid range which is obtained by frequency doubling with the first nonlinear crystal 16 is in a range of approx. 1040 nm to approx. 1080 nm. As the laser oscillating source 10, any device capable of outputting the beam of the wavelength $\lambda 1$ in the above range is used. In light of a coagulation efficiency, it is preferable to output the orange beam of a wavelength in a range of approx. 580 nm to approx. 600 nm. Therefore the wavelength $\lambda 2$ for generating the orange beam of the wavelength $\lambda 2'$ in the aforesaid range which is obtained by frequency doubling with the second nonlinear crystal 26 is in a range of approx. 1160 nm to approx. 1200 nm. The use of the fiber mentioned above enables the efficient generation of the first-order Stokes beam of the wavelength $\lambda 2$ in the range of approx. 1160 nm to approx. 1200 nm by the stimulated Raman scattering of 925 cm$^{-1}$ by input of the excitation beam of the wavelength $\lambda 1$ in the range of approx. 1040 nm to approx. 1080 nm. Further, for the photocoaglation treatment, the apparatus is desired to be able to output the red beam of a wavelength in a range of approx. 610 nm to approx. 630 nm. Therefore the wavelength $\lambda 3$ for generating the red beam of the wavelength $\lambda 3'$ in the aforesaid range which is obtained by frequency doubling with the third nonlinear crystal 36 is in a range of approx. 1220 nm to approx. 1260 nm. In this respect, similarly, the use of the fiber mentioned above enables the efficient generation of the second-order Stokes beam of the wavelength $\lambda 3$ in the range of approx. 1220 nm to approx. 1260 nm by the stimulated Raman scattering of 408 cm$^{-1}$ by input of the excitation beam of the wavelength $\lambda 1$ in the range of approx. 1040 nm to approx. 1080 nm. The laser oscillating source 10 which emits the $\lambda 1$-beam for the above purpose is not limited to the above mentioned Nd:YAG laser and Nd:YLF laser, and may be any appropriate one. For example, a Yb-doped fiber laser can be used suitably. This Yb fiber laser outputs a beam of a wavelength $\lambda 1$ (approx. 1064 nm).

With the apparatus in the present embodiment using the Raman fiber, it is possible to generate the orange beam effective particularly in the ophthalmic treatment and to generate the green beam and the red beam of a relatively shorter wavelength at high output power by a single apparatus. The apparatus can selectively output those beams. This makes it possible to expand its applicability to treatments.

Figure 3:
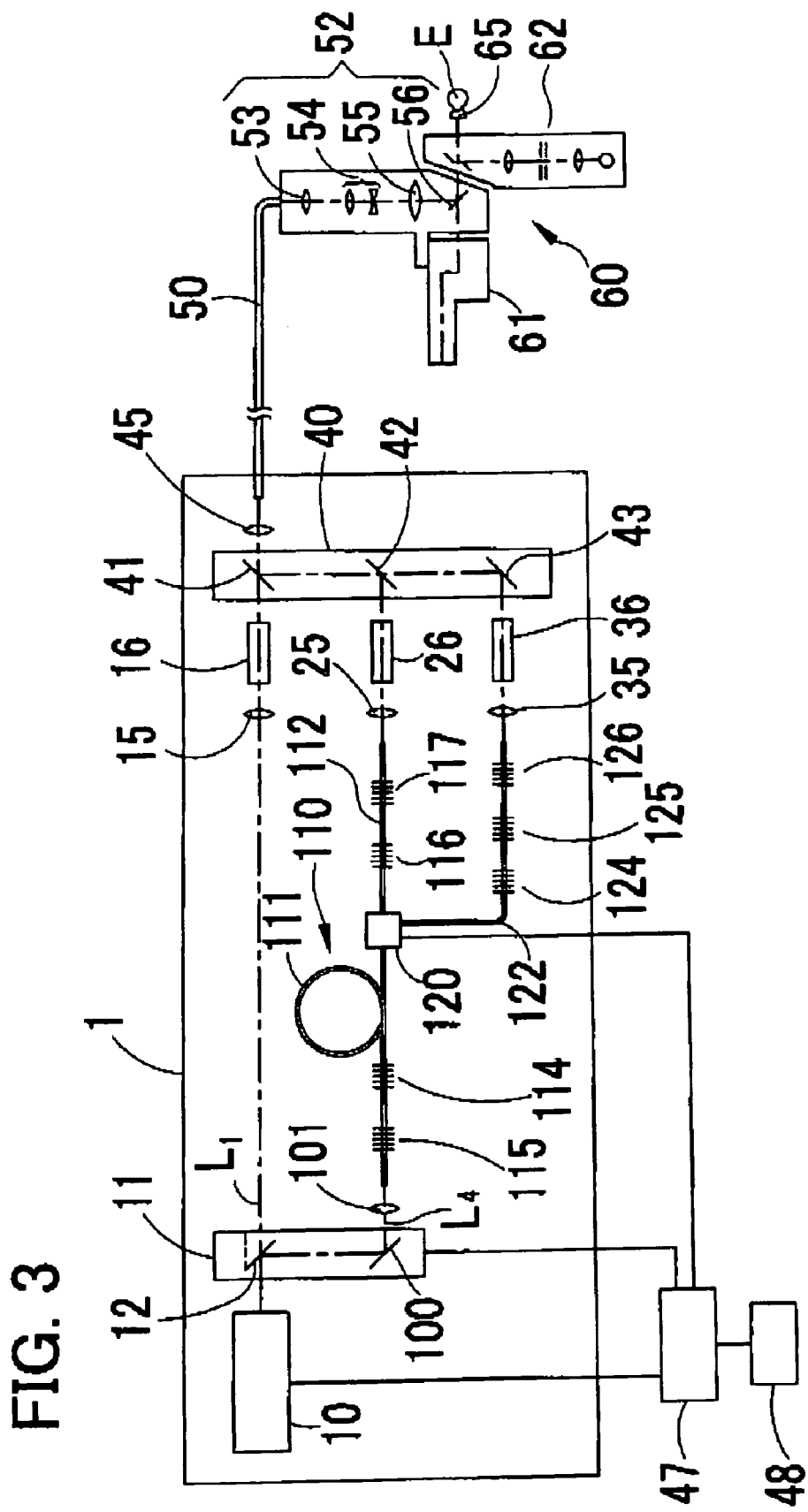
FIG. 3 is a schematic structural view of a laser apparatus for an ophthalmic treatment in a second embodiment.

FIG. 3 is a schematic structure of a laser apparatus for an ophthalmic treatment in a second embodiment. Elements similar to those shown in FIG. 1 are identified by similar numerals. In the second embodiment, a part of a single fiber-based Raman wavelength shifter (converter) is used in common for selectively generating Stokes beams of the wavelengths $\lambda 2$ and $\lambda 3$.

In FIG. 3, the input switching unit 11 includes a mirror 12 and a mirror 100 placed in a reflected path of light by the mirror 12. When the mirror 12 is set in the optical path, the $\lambda 1$-beam is directed to the optical path L4. In this optical path L4, there are placed a condensing lens 101 and a fiber-based Raman wavelength shifter (converter) 110. This shifter 110 is provided with a TiO$_2$-doped, SiO$_2$-based optical fiber 111 as with the optical fiber 21. The optical fiber 111 is 6 μm in core diameter and approx. 500 m or more in length. The optical fiber 111 is connected to an optical fiber switch 120 which is connected, at its output part, to similarly two TiO$_2$-doped, SiO$_2$-based optical fibers 112 and 122. The optical fiber switch 120 is used to selectively connect the optical fiber 111 to the optical fiber 112 or the optical fiber 122 and thus to selectively switch between a fiber-based first Raman wavelength shifter generating the first-order Stokes beam of the wavelength λ2 and a fiber-based second Raman wavelength shifter generating the second-order Stokes beam of the wavelength λ3.

In the optical fiber 111, there are formed an FBG 114 having high reflectivity (99% or more reflectivity) which reflects the first-order Stokes beam of the wavelength λ2 generated by the stimulated Raman scattering and an FBG 115 having high reflectivity (99% or more reflectivity) which reflects the second-order Stokes beam of the wavelength λ3.

In the optical fiber 112, on the other hand, an FBG 116 used in a pair with the FBG 114 and an FBG 117 which reflects the λ1-beam while allowing the λ2-beam to pass therethrough. The FBG 116 has 85% or less reflectivity to the λ2-beam and acts as an output coupler. The optical fiber 122 is formed with an FBG 124 having high reflectivity (99% or more reflectivity) used in a pair with the FBG 114, an FBG 125 used in a pair with the FBG 115, and an FBG 126 which reflects the λ1-beam while allowing the λ3-beam to pass therethrough. The FBG 126 has 85% or less reflectivity to the λ3-beam and acts as an output coupler.

With the above structure, when "orange" is selected with the switch on the control panel 48, the mirror 12 is set in the optical path and the optical fiber switch 120 is driven to connect the optical fiber 111 to the optical fiber 112. The λ1-beam from the laser oscillating source 10 is guided to the Raman wavelength shifter 110, in which the first-order Stokes beam of the wavelength λ2 is generated. For this λ2-beam, the FBG 114 having high reflectivity and the FBG 116 allowing a part of the beam to pass therethrough form a resonator, picking up the λ2-beam. The λ2-beam having passed through the FBG 116 passes through the condensing lens 25 and enters the second nonlinear crystal 26 in the same way as above. The λ2-beam is then wavelength-converted to the second-harmonic orange beam of the wavelength λ2'. In this way, the laser oscillator 1 outputs the orange beam.

When "red" is selected with the switch on the control panel 48, the optical fiber switch 120 is driven to connect the optical fiber 111 to the optical fiber 122. The λ1-beam from the laser oscillating source 10 is guided to the Raman wavelength shifter 110, in which the first-order Stokes beam of the wavelength λ2 is generated. For this λ2-beam, the FBG 114 of high reflectivity and the FBG 124 of high reflectivity form a resonator which therein confines the λ2-beam. Accordingly, the second-order Stokes beam of the wavelength λ3 is further generated. For this λ3-beam, the FBG 116 of high reflectivity and the FBG 125 which allows a part of the beam to pass therethrough form a resonator, picking up the λ3-beam. This λ3-beam passes through the FBG 126 and then, in the same way as above, passes through the condensing lens 35 and enters the third nonlinear crystal 36. The λ3-beam is then wavelength-converted to the second-harmonic red beam of the wavelength λ3'. Thus, the laser oscillator 1 outputs the red beam. It is to be noted that, in the case that "green" is selected with the switch on the control panel 48, the laser oscillator 1 outputs the green beam as in the case of FIG. 1.

Figure 4:
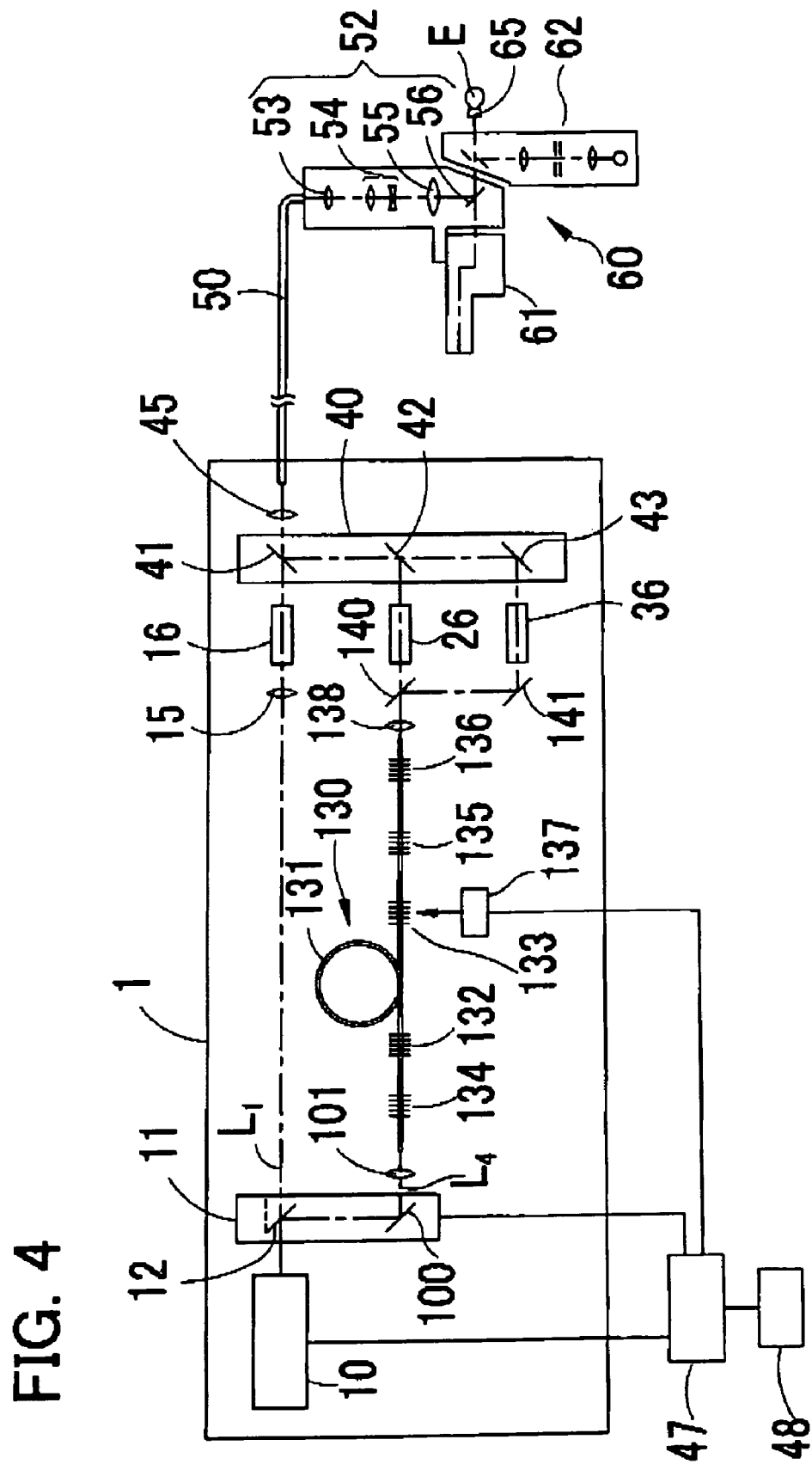
FIG. 4 is a schematic structural view of a laser apparatus for an ophthalmic treatment in a third embodiment.

FIG. 4 is a schematic structural view of a laser apparatus for an ophthalmic treatment in a third embodiment. Elements similar to those shown in FIGS. 1 and 3 are identified by similar numerals. In the third embodiment, a single fiber-based Raman wavelength shifter (converter) is used in common for selectively generating two Stokes beams of the wavelengths λ2 and λ3.

In FIG. 4, a condensing lens 101 and a fiber-based Raman wavelength shifter (converter) 130 are placed in an optical path L4. This Raman wavelength shifter 130 is provided with a $TiO_2$-doped, $SiO_2$-based optical fiber 131. The optical fiber 131 is 6 μm in core diameter and approx. 500 m or more in length. The optical fiber 131 is formed with a pair of FBGs 132 and 133 which forms a resonator for the first-order Stokes beam of the wavelength λ2 generated by the stimulated Raman scattering and another pair of FBGs 134 and 135 which forms a resonator for the second-order Stokes beam of the wavelength λ3 generated by the stimulated Raman scattering. There is further formed an FBG 136 which reflects the λ1-beam while allowing the λ2- and λ3-beams to pass therethrough.

The FBG 132 formed in the input section has high reflectivity (99% or more reflectivity) to the λ2-beam and the FBG 134 formed in the same input section has high reflectivity (99% or more reflectivity) to the λ3-beam. The FBG 133 formed in the output section has adjustable reflectivity in a range of 10% to 100% to the λ2-beam. An adjusting unit 187 thermally or mechanically adjusts the reflectivity of the FBG 133 to the λ2-beam. The FBG 135 has 85% or less reflectivity to the λ3-beam. The reflectivity of the FBG 135 that acts as an output coupler is so chosen as to achieve optimum output power at the λ3-beam.

In an optical path following the output end of the optical fiber 131, there are placed a condensing lens 138 and a dichroic mirror 140 which allows the λ2-beam to pass therethrough while reflecting the λ3-beam. The λ2-beam having passed through the dichroic mirror 140 is guided to the second nonlinear crystal 26. A mirror 141 is placed in a reflected path of light by the dichroic mirror 140. The λ3-beam reflected by the dichroic mirror 140 and the mirror 141 in turn is directed to the third nonlinear crystal 36.

With the above structure, when "orange" is selected with the switch on the control panel 48, the mirror 12 is set in the optical path and the adjusting unit 137 is driven to adjust the reflectivity of the FBG 133 to the λ2-beam to low reflectivity (e.g., 50%). The λ1-beam from the laser oscillating source 10 is guided to the Raman wavelength shifter 130, in which the first-order Stokes beam of the wavelength λ2 is generated. For this λ2-beam, the FBG 132 having high reflectivity and the FBG 133 allowing a part of the beam to pass therethrough form a resonator, picking up the λ2-beam. This λ2-beam passes through the FBGs 135 and 136 and then is outputted from the optical fiber 131. Thereafter, the λ2-beam enters the second nonlinear crystal 26 through the condensing lens 138 and is wavelength-converted to the second-harmonic orange beam of the wavelength λ2'.

When "red" is selected with the switch on the control panel 48, the adjusting unit 137 is driven to adjust the reflectivity of the FBG 133 to the λ2-beam to high reflectivity (99% or more). The λ1-beam from the laser oscillating source 10 is guided to the Raman wavelength shifter 130, in which the first-order Stokes beam of the wavelength λ2 is generated. For this λ2-beam, the FBG 132 of high reflectivity and the FBG 133 of high reflectivity form a resonator, which therein confines the λ2-beam. Accordingly, the second-order Stokes beam of the wavelength λ3 is further generated. For the λ3-beam, the FBG 134 having high reflectivity and the FBG 135 allowing a part of the beam to pass therethrough form a resonator, picking up the λ3-beam. The λ3-beam passes through the FBG 136 and is outputted from the optical fiber 131. This λ3-beam then passes through the condensing lens 138, the dichroic mirror 140, and the mirror 141 in order and enters the third nonlinear crystal 36 in which the λ3-beam is then wavelength-converted to the second-harmonic red beam of the wavelength λ3'. Consequently, the laser oscillator 1 outputs the red beam.

Figure 5:
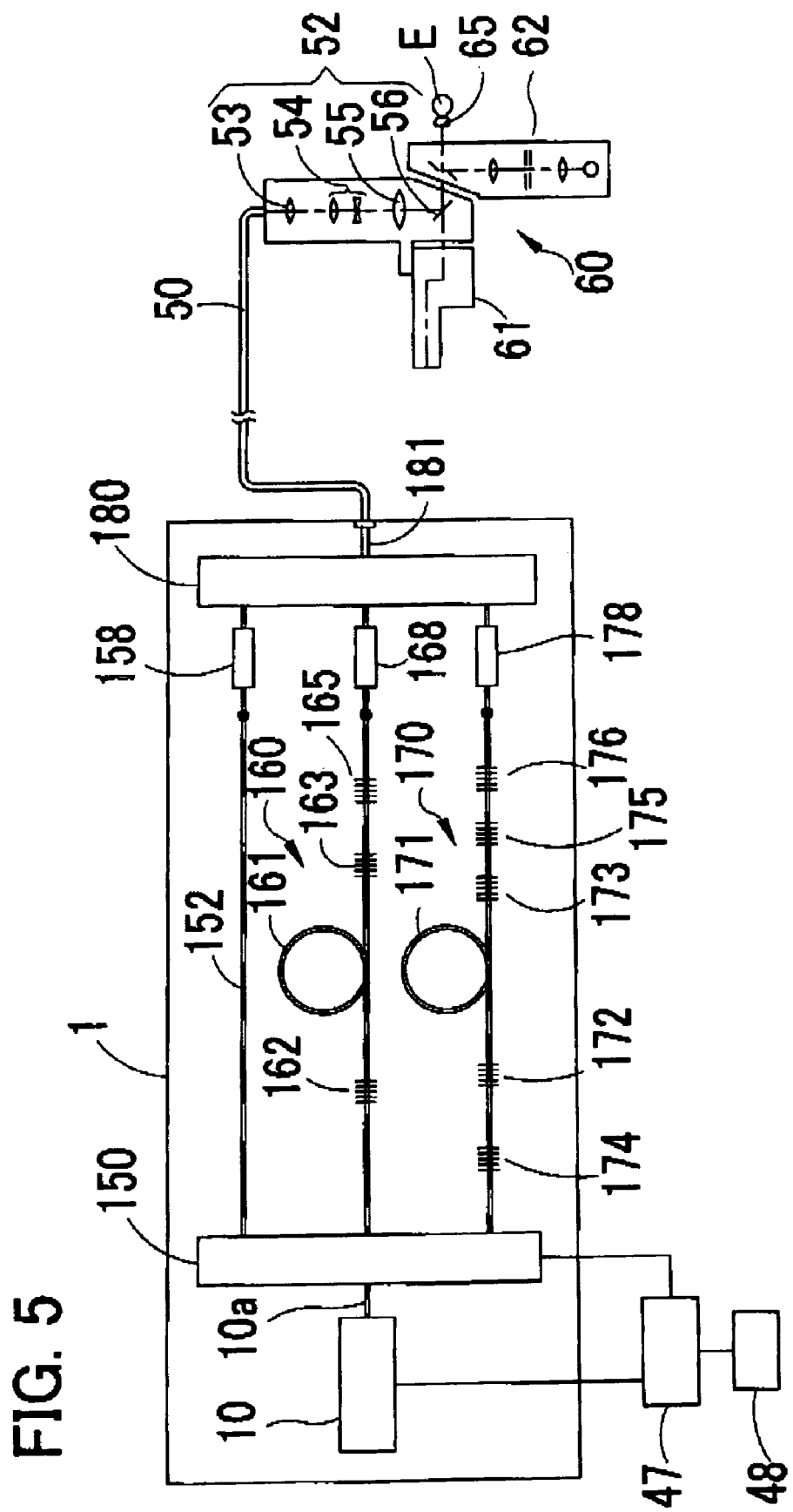
FIG. 5 is a schematic structural view of a laser apparatus for an ophthalmic treatment in a fourth embodiment.

FIG. 5 is a schematic structural view of a laser apparatus for an ophthalmic treatment in a fourth embodiment. Elements similar to those shown in FIG. 1 are identified by similar numerals. In the fourth embodiment, all optical systems following the laser oscillating source 10 in the laser oscillator 1 are constructed using fiber optical systems.

In FIG. 5, the λ1-beam from the laser oscillating source 10 is inputted into a first fiber switch 150 through a fiber 10a. The fiber switch 150 includes a 1-input and 3-output parts to switch among the three output paths. A first output part of the fiber switch 150 is connected to an extending optical fiber 152 of which an output end is connected to an input fiber of a periodically-poled nonlinear crystal (corresponding to a "second nonlinear crystal" in claims) 158 of a wave guide type. An output fiber of the nonlinear crystal 158 is connected to a second fiber switch 180 which is a switch including a 3-input and 1-output parts of which an output end is connected to a fiber 181. This fiber 181 is capable of being coupled to the optical fiber 50 which transmits a beam to the light guiding optical system 52.

A second output part of the fiber switch 150 is connected to an input end of an optical fiber 161 constituting a fiber-based Raman wavelength shifter (converter) 160. The optical fiber 161 is made of the same material as the optical fiber 21 in the aforementioned embodiments. The optical fiber 161 is formed with a pair of FBGs 162 and 163 which forms a resonator for the first-order Stokes beam of the wavelength λ2 and an FBG 165 which reflects the λ1-beam while allowing the λ2-beam to pass therethrough. An output end of the optical fiber 161 is connected to an input fiber of a nonlinear crystal (corresponding to a "first nonlinear crystal" in claims) 168 of a wave guide type. An output fiber of the nonlinear crystal 168 is connected to the second fiber switch 180.

A third output part of the fiber switch 150 is connected to an input end of an optical fiber 171 constituting a fiber-bared Raman wavelength shifter (converter) 170. The optical fiber 171 is also made of the same material as the optical fiber 21 in the aforementioned embodiments. The optical fiber 171 is formed with a pair of FBGs 172 and 173 which forms a resonator for the first-order Stokes beam of the wavelength λ2, another pair of FBGs 174 and 175 which forms a resonator for the second-order Stokes beam of the wavelength λ3, and an FBG 176 which reflects the λ1-beam while allowing the λ3-beam to pass therethrough. An output end of the optical fiber 171 is connected to an input fiber of a nonlinear crystal 178 of a wave guide type. An output fiber of the nonlinear crystal 178 is connected to the second fiber switch 180.

With the above structure, when the wavelength (color) to be used for a treatment is selected with the switch on the control panel 48, the control unit 47 selectively switches the output part of the first fiber switch 150 and the input part of the second fiber switch 180 respectively to appropriate configurations. The λ1-beam from the laser oscillating source 10 is inputted into one of the optical fibers 152, 161, and 171 in accordance with the switching. The λ1-beam inputted into the optical fiber 152 is converted to the green beam of the wavelength λ1' by the first nonlinear crystal 158. The λ1-beam inputted into the optical fiber 161 is shifted to the λ2-beam by the stimulated Raman scattering and then converted to the orange beam of the wavelength λ2' by the second nonlinear crystal 168. The λ1-beam inputted into the optical fiber 171 is shifted to the λ2-beam and further shifted to the λ3-beam by the stimulated Raman scattering. This λ3-beam is then converted to the red beam of the wavelength λ3' by the third nonlinear crystal 178.

In the laser oscillator 1 in the fourth embodiment, each optical element in the optical paths of the beams outputted from the laser oscillating source 10 and inputted into the optical fiber 50 is connected to one another by the fiber optical systems. Accordingly, the alignment problem of each optical element can be reduced and a reliable laser apparatus can be realized. It is more effective if a fiber laser such as a Yb fiber laser is used as the laser oscillating source 10.

In the fourth embodiment, as in the case of the first and third embodiments, the Raman wavelength shifter 160 and the Raman wavelength shifter 170 may be used partially or entirely in common.

The laser apparatus for an ophthalmic treatments is explained in the above embodiments, but the present invention can be applied to a laser apparatus for a dermatological treatment.

While the presently preferred embodiment of the present invention has been shown and described, it is to be understood that this disclosure is for the purpose of illustration and that various changes and modifications may be made without departing from the scope of the invention as set forth in the appended claims.

What is claimed is:

1. A medical laser apparatus comprising:
   a solid laser oscillating source which emits a beam of a wavelength λ1 in an infrared region of approx. 1040 nm to approx. 1080 nm;
   a first fiber-based Raman shifter including a first Raman fiber which generates, when receives the λ1-beam from the laser oscillating source, a first-order Stokes beam of a wavelength λ2 different from the wavelength λ1 by stimulated Raman scattering, the first Raman fiber being formed with a pair of fiber Bragg gratings which forms a resonator for the λ2-beam;
   a first nonlinear crystal which wavelength-converts the λ2-beam outputted from the first Raman wavelength shifter to a second harmonic beam of a wavelength λ2' in an orange region of approx. 580 nm to approx. 600 nm; and
   a light guiding optical system which guides the λ2'-beam to a treatment part.

2. The medical laser apparatus according to claim 1, wherein the Raman fiber includes a silica($SiO_2$)-based optical fiber doped with titanium oxide ($TiO_2$).

3. The medical laser apparatus according to claim 1, further comprising:
- a second nonlinear crystal which wavelength-converts the $\lambda 1$-beam from the laser oscillating source to a second harmonic beam of a wavelength $\lambda 1'$ in a green region of approx. 520 nm to approx. 540 nm;
- an input switching unit which selectively switches input of the $\lambda 1$-beam from the laser oscillating source into between the second nonlinear crystal and the first Raman wavelength shifter; and
- an output switching unit which selectively switches between output of the $\lambda 1'$-beam from the second nonlinear crystal to the light guiding optical system and output of the $\lambda 2'$-beam from the first nonlinear crystal to the light guiding optical system; and
- wherein the light guiding optical system is also adapted to guide the $\lambda 1'$-beam to the treatment part.

4. The medical laser apparatus according to claim 3, wherein the input switching unit and the output switching unit include a fiber switch.

5. The medical laser apparatus according to claim 1, further comprising:
- a second fiber-based Raman shifter including a second Raman fiber which generates, when receiving the $\lambda 1$-beam from the laser oscillating source, the first-order Stokes beam of the wavelength $\lambda 2$ and further a second-order Stokes beam of a wavelength $\lambda 3$ different from the wavelengths $\lambda 1$ and $\lambda 2$ by the stimulated Raman scattering, the second Raman fiber being formed with two pairs of fiber Bragg gratings which form resonators for the $\lambda 2$-beam and the $\lambda 3$-beam, respectively;
- a third nonlinear crystal which wavelength-converts the $\lambda 3$-beam outputted from the second Raman wavelength shifter to a second harmonic beam of a wavelength $\lambda 3'$ in a red region of approx. 610 nm to approx. 630 nm;
- an input switching unit which selectively switches input of the $\lambda 1$-beam from the laser oscillating source into between the first Raman wavelength shifter and the second Raman wavelength shifter;
- an output switching unit which selectively switches between output of the $\lambda 2'$-beam from the first nonlinear crystal to the light guiding optical system and output of the $\lambda 3'$-beam from the third nonlinear crystal to the light guiding optical system; and
- wherein the light guiding optical system is also adapted to guide the $\lambda 3'$-beam to the treatment part.

6. The medical laser apparatus according to claim 5, wherein the second Raman fiber uses at least a part of the first Raman fiber in common.

7. The medical laser apparatus according to claim 5, wherein the input switching unit and the output switching unit include a fiber switch.

8. The medical laser apparatus according to claim 1, wherein the laser oscillating source includes an Nd:YAG laser, an Nd:YLF laser, or a Yb-doped fiber laser.

\* \* \* \* \*